(12) United States Patent
Pak (10) Patent No.: US 9,067,198 B2
(45) Date of Patent: Jun. 30, 2015

(54) CALCINATION PROCESS FOR PRODUCING AN IMPROVED ETHYLENE OXIDE CATALYST

(71) Applicant: Scientific Design Company, Inc., Little Ferry, NJ (US)

(72) Inventor: Serguei Pak, Teaneck, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days.

(21) Appl. No.: 14/144,747

(22) Filed: Dec. 31, 2013

(65) Prior Publication Data

US 2014/0187417 A1 Jul. 3, 2014

Related U.S. Application Data

(60) Provisional application No. 61/747,519, filed on Dec. 31, 2012.

(51) Int. Cl.

| | |
|---|---|
| *B01J 21/00* | (2006.01) |
| *B01J 21/04* | (2006.01) |
| *B01J 20/00* | (2006.01) |
| *B01J 23/00* | (2006.01) |
| *B01J 23/02* | (2006.01) |

(Continued)

(52) U.S. Cl.
CPC ..................................... *B01J 23/688* (2013.01)

(58) Field of Classification Search
USPC .......... 502/243, 327, 348, 355, 415, 439, 347
See application file for complete search history.

(56) References Cited

U.S. PATENT DOCUMENTS

| 4,226,782 A | 10/1980 | Hayden et al. |
| 4,242,235 A | 12/1980 | Cognion et al. |

(Continued)

FOREIGN PATENT DOCUMENTS

KR     1020080005505     1/2008

OTHER PUBLICATIONS

International Search Report dated Apr. 25, 2014, received in a corresponding foreign application.

(Continued)

*Primary Examiner* — Cam N. Nguyen
(74) *Attorney, Agent, or Firm* — Scully, Scott, Murphy & Presser, P.C.

(57) ABSTRACT

A method for producing a catalyst effective in the oxidative conversion of ethylene to ethylene oxide, the method comprising subjecting a refractory carrier impregnated with a liquid silver-containing solution to a calcination process, wherein the calcination process comprises a solvent removal step in which the silver-impregnated carrier is heated to a base temperature ($T_{base}$) of at least 80° C. and up to about 200° C. to produce a dry carrier impregnated with ionic silver, followed by a silver reduction step in which the dry carrier is gradually heated above the base temperature to a maximum temperature ($T_{max}$) of at least 350° C. and up to about 500° C. and then gradually cooled to the base temperature, wherein the method is conducted such that $(T_{base}-T_{max}) \times HW$ is at least 2000 min.° C. wherein HW is a full width at half maximum of a temperature versus time curve delineated by the silver reduction step.

24 Claims, 4 Drawing Sheets

(51) Int. Cl.
  *B01J 23/08* (2006.01)
  *B01J 23/40* (2006.01)
  *B01J 23/42* (2006.01)
  *B01J 23/48* (2006.01)
  *B01J 23/68* (2006.01)

(56) References Cited

U.S. PATENT DOCUMENTS

| | | | |
|---|---|---|---|
| 4,248,741 A | 2/1981 | Wernli et al. | |
| 4,761,394 A | 8/1988 | Lauritzen | |
| 4,766,105 A | 8/1988 | Lauritzen | |
| 4,908,343 A | 3/1990 | Bhasin | |
| 5,011,807 A | 4/1991 | Hayden et al. | |
| 5,057,481 A | 10/1991 | Bhasin | |
| 5,077,256 A * | 12/1991 | Yamamoto et al. | 502/243 |
| 5,099,041 A | 3/1992 | Hayden et al. | |
| 5,102,848 A | 4/1992 | Soo et al. | |
| 5,187,140 A | 2/1993 | Thorsteinson et al. | |
| 5,266,548 A | 11/1993 | Koradia et al. | |
| 5,364,826 A * | 11/1994 | Kemp | 502/315 |
| 5,380,697 A * | 1/1995 | Matusz et al. | 502/348 |
| 5,395,812 A * | 3/1995 | Nagase et al. | 502/238 |
| 5,407,888 A | 4/1995 | Herzog et al. | |
| 5,418,202 A * | 5/1995 | Evans et al. | 502/348 |
| 5,545,603 A * | 8/1996 | Kemp | 502/347 |
| 5,597,773 A | 1/1997 | Evans et al. | |
| 5,663,385 A * | 9/1997 | Kemp | 549/536 |
| 5,705,661 A * | 1/1998 | Iwakura et al. | 549/536 |
| 5,739,075 A * | 4/1998 | Matusz | 502/302 |
| 5,801,259 A * | 9/1998 | Kowaleski | 549/536 |
| 5,831,037 A | 11/1998 | Ohsuga et al. | |
| 5,929,259 A * | 7/1999 | Lockemeyer | 549/534 |
| 6,511,938 B1 | 1/2003 | Liu et al. | |
| 6,579,825 B2 * | 6/2003 | Lockemeyer | 502/347 |
| 6,831,037 B2 | 12/2004 | Szymanski et al. | |
| 7,247,600 B2 * | 7/2007 | Lockemeyer | 502/347 |
| 7,485,597 B2 * | 2/2009 | Lockemeyer et al. | 502/216 |
| 7,553,980 B2 * | 6/2009 | Rizkalla et al. | 549/536 |
| 7,655,596 B2 * | 2/2010 | Zhang et al. | 502/348 |
| 7,932,408 B2 * | 4/2011 | Guckel | 549/536 |
| 7,977,274 B2 * | 7/2011 | Gueckel | 502/243 |
| 8,084,390 B2 * | 12/2011 | Gerdes et al. | 502/347 |
| 8,546,297 B2 * | 10/2013 | Rokicki et al. | 502/347 |
| 8,883,675 B2 * | 11/2014 | Rizkalla et al. | 502/348 |
| 2004/0110973 A1 | 6/2004 | Matusz | |
| 2005/0096219 A1 | 5/2005 | Szymanski et al. | |
| 2006/0252643 A1 * | 11/2006 | Pak | 502/439 |
| 2007/0207914 A1 * | 9/2007 | Lockemeyer | 502/11 |
| 2008/0039316 A1 | 2/2008 | Bhise et al. | |
| 2009/0264678 A1 * | 10/2009 | Lockemeyer et al. | 564/475 |
| 2010/0191006 A1 * | 7/2010 | Guckel | 549/536 |
| 2010/0298128 A1 | 11/2010 | Serafin et al. | |
| 2011/0152073 A1 * | 6/2011 | Dialer et al. | 502/347 |
| 2011/0281724 A1 * | 11/2011 | Rizkalla et al. | 502/347 |

OTHER PUBLICATIONS

Drake, L.C., et al., "Macropore-Size Distributions in Some Typical Porous Substances", Ind. Eng. Chem. Anal. Ed., Publication Date: Dec. 1945, 17 (12), pp. 787-791.

Brunauer, S., et al., "Adsorption of Gases in Multimolecular Layers", J. Am. Chem. Soc., Feb. 1938, pp. 309-316.

* cited by examiner

CALCINATION PROCESS FOR PRODUCING AN IMPROVED ETHYLENE OXIDE CATALYST

CROSS REFERENCE TO RELATED APPLICATION

The present invention claims the benefit of U.S. Provisional Patent Application No. 61/747,519 filed Dec. 31, 2012, the entire content and disclosure of which is incorporated herein by reference.

FIELD OF THE INVENTION

The present disclosure relates to silver-based ethylene oxide catalysts for the oxidative conversion of ethylene to ethylene oxide, and in particular, to their preparation. More particularly, the present disclosure relates to a process for calcining a high selectivity silver-based ethylene oxide catalyst.

DESCRIPTION OF THE RELATED ART

As known in the art, high selectivity catalysts (HSCs) for the epoxidation of ethylene refer to those catalysts that possess selectivity values higher than high activity catalysts (HACs) used for the same purpose. Both types of catalysts include silver as the active catalytic component on a refractory support (i.e., "carrier", such as alumina). Typically, one or more promoters are included in the catalyst to improve or adjust properties of the catalyst, such as selectivity.

Generally, HSCs achieve the higher selectivity (typically, in excess of 87 mole % or above) by incorporation of rhenium as a promoter. Typically, one or more additional promoters selected from alkali metals (e.g., cesium), alkaline earth metals, transition metals (e.g., tungsten compounds), and main group metals (e.g., sulfur and/or halide compounds) are also included.

There are also ethylene epoxidation catalysts that may not possess the selectivity values typically associated with HSCs, though the selectivity values are improved over HACs. These types of catalysts can also be considered within the class of HSCs, or alternatively, they can be considered to belong to a separate class, e.g., "medium selectivity catalysts" or "MSCs." These types of catalysts may exhibit selectivities of at least 83 mole % and up to 87 mole %.

In contrast to HSCs and MSCs, the HACs are ethylene epoxidation catalysts that generally do not include rhenium, and for this reason, do not provide the selectivity values of HSCs or MSCs. Typically, HACs include cesium (Cs) as the only promoter.

It is well known that with use of a catalyst, the catalyst will age (i.e., degrade) until use of the catalyst is no longer practical, i.e., when activity and selectivity values diminish to a level that is no longer industrially efficient or economical. Thus, there is a continuous effort to extend the useful lifetime (i.e., "longevity" or "usable life") of these catalysts by maintaining an effective level of activity and selectivity characteristics. The useful lifetime of the catalyst is directly dependent on the stability of the catalyst. As used herein, the "useful lifetime" is the time period for which a catalyst can be used until one or more functional parameters, such as selectivity or activity, degrade to such a level that use of the catalyst becomes impractical.

It is known in the art that, while the selectivity of HSCs is generally acceptable to the industry, their useful lifetime can use improvement. For example, while HACs typically last between 24 and 36 months, HSCs are often useful for less than 24 months, usually because of an unacceptable loss of selectivity and/or activity.

Stability of the catalyst has largely been attributed to various characteristics of the carrier. Some characteristics of the carrier that have undergone much research include surface area, porosity, and pore volume distribution, among others. The preparation and modification of alumina carriers for enhancing ethylene epoxidation catalyst performance are described, for example, in U.S. Pat. Nos. 4,226,782, 4,242,235, 5,266,548, 5,380,697, 5,597,773, 5,831,037 and 6,831,037 as well as in U.S. Patent Application Publication Nos. 2004/0110973 A1 and 2005/0096219 A1.

However, there remains a need in the art for further improvements in the stability of ethylene epoxidation catalysts, as well as improvements in selectivity and activity values. There would be a particular advantage in a method that could improve the stability and other characteristics of such catalysts by modifying the carrier by means that are facile and economically feasible.

SUMMARY

The present disclosure describes a process for improving the activity, selectivity, or stability of a silver-based catalyst useful in the conversion of ethylene to ethylene oxide. In the process, conditions used in the calcination process are carefully selected and controlled to achieve the improved catalyst. In particular, the calcination process described herein is at least a two-step process in which, in a first step, a carrier impregnated with a liquid silver-containing solution (i.e., first catalyst precursor) is heated in order to effect solvent removal to form a dried silver-impregnated carrier (i.e., second catalyst precursor), and in a second step, the dried silver-impregnated carrier is further heated to a higher temperature in order to effect silver reduction to produce the final catalyst. The ultimate (maximum) temperature and temperature ramp rate employed in each step are carefully selected to provide a silver-based catalyst improved in activity, selectivity, or stability.

The instant disclosure provides the particularly surprising result that, by use of the two-step process, and by lengthening the time of at least one of the heating steps (i.e., reducing the temperature ramp rate) in conjunction with controlling the maximum temperature, a silver-based catalyst improved in activity, selectivity, or stability is achieved relative to a catalyst calcined by a conventional process in which the precursor is calcined in a single step or in which the residence time of one or both of the heating steps is less than that employed in the instantly described process. In particular embodiments, the calcination process involves subjecting the silver-impregnated carrier to a solvent removal step in which the silver-impregnated carrier is heated to a base temperature ($T_{base}$) of at least 80° C. and up to about 200° C. for a period of time sufficient to result in a dry carrier impregnated with ionic silver, followed by a silver reduction step in which the dry impregnated carrier is gradually heated above the base temperature under an inert atmosphere to a maximum temperature ($T_{max}$) of at least 350° C. and up to about 500° C. and then gradually cooled to the base temperature. Preferably, the process is conducted such that $(T_{base}-T_{max}) \times HW$ is at least 2000 min.° C., wherein $T_{base}$ and $T_{max}$ are measured in ° C., and HW is measured in minutes and is a full width at half maximum of a temperature versus time curve delineated by the silver reduction step where $T_{base}$ is taken as the baseline of the curve in calculating HW.

DETAILED DESCRIPTION

As used herein, the term "about" generally indicates within ±0.5, 1, 2, 5, or 10% of the indicated value. For example, in its broadest sense, the phrase "about 100° C." can mean 100° C.±10%, which indicates 100±10° C. or 90-110° C.

The carrier, which is typically porous, may be selected from any of the solid refractory carriers known in the art for use in silver-based catalysts. Some examples of carrier materials include alumina (e.g., alpha-alumina), charcoal, pumice, magnesia, zirconia, titania, kieselguhr, fuller's earth, silicon carbide, silica, silicon carbide, clays, artificial zeolites, natural zeolites, silicon dioxide and/or titanium dioxide, ceramics, and combinations thereof.

In a particular embodiment, the carrier includes or is completely composed of alumina, which may be a single type of alumina (e.g., alpha-alumina) or mixture of alumina compositions (e.g., gamma- and alpha-alumina). The alpha-alumina preferably has a high purity, i.e., about 95 wt % or more, and more preferably, 98 wt % or more alpha-alumina. The alpha-alumina carrier may or may not also include inorganic oxides other than alpha-alumina, such as silica, alkali metal oxides (e.g., sodium oxide) and trace amounts of other metal-containing or non-metal-containing additives or impurities. In some embodiments, the alpha-alumina is a low sodium alumina or a low sodium reactive alumina. The term "reactive alumina" as used herein generally indicates an alpha-alumina with good sinterability and having a fine particle size, generally, of 2 microns or less. Generally, a "low sodium alumina" material contains 0.1% or less sodium content. Alternatively, or in addition, a "low sodium alumina" can indicate an alumina material having 0.1 mg or less of sodium. Good sinterability is generally derived from a particle size of 2 microns or less. The carrier may be produced by conventional techniques well known to those skilled in the art, such as by combining alumina microparticles, a solvent (e.g., water), a temporary binder or burnout material, a permanent binder, and/or a porosity controlling agent, and then shaping, molding, or extruding the resulting paste, before firing (i.e., calcining) the preform by methods well known in the art. Alternatively, the carrier may be purchased from a catalyst carrier provider.

The carrier precursor particles can be of any suitable size, and are typically microparticles. In different embodiments, the carrier microparticles can have a particle size (i.e., diameter, if substantially spherical) of precisely, about, at least, greater than, up to, or less than, for example, 1, 2, 3, 4, 5, 6, 7, 8, 9, 10, 12, 15, or 20 microns (μm), or the carrier microparticles may have a size within a range bounded by any two of the foregoing exemplary values. The carrier precursor particles may also be composed of two or more portions of microparticles of different sizes or size ranges, typically selected from the above exemplary sizes. Moreover, each portion of the carrier precursor particles may be in a suitable weight percentage by total weight of carrier precursor or finished carrier (before silver impregnation). In different embodiments, one or more portions of carrier microparticles in different size ranges may be present in an amount of precisely, about, at least, greater than, up to, or less than, for example, 1 wt %, 2 wt %, 5 wt %, 20 wt %, 25 wt %, 30 wt %, 40 wt %, 50 wt %, 60 wt %, 70 wt %, 80 wt %, 90 wt %, 95 wt %, 98 wt %, or 99 wt %, or within a weight percentage (wt %) range bounded by any of the foregoing values.

The carrier can be porous or non-porous, but is preferably porous, typically with a B.E.T. surface area of at most 20 $m^2/g$. The B.E.T. surface area is more typically in the range of about 0.1 to 10 $m^2/g$, and more typically from 1 to 5 $m^2/g$. In other embodiments, the carrier is characterized by a B.E.T. surface area of about 0.3 $m^2/g$ to about 3 $m^2/g$, preferably about 0.6 $m^2/g$ to about 2.5 $m^2/g$, and more preferably about 0.7 $m^2/g$ to about 2.0 $m^2/g$. The B.E.T. surface area described herein can be measured by any suitable method, but is more preferably obtained by the method described in Brunauer, S., et al., *J. Am. Chem. Soc.*, 60, 309-16 (1938). The final carrier typically possesses a water absorption value (water pore volume) ranging from about 0.10 cc/g to about 0.80 cc/g, more typically from about 0.2 cc/g to about 0.8 cc/g, and more typically from about 0.25 cc/g to about 0.6 cc/g.

The carrier, if porous, can have any suitable distribution of pore diameters. As used herein, the term "pore diameter" is meant to indicate a pore size. The pore volume (and pore size distribution) described herein can be measured by any suitable method, such as by the conventional mercury porosimeter method described in, for example, Drake and Ritter, *Ind. Eng. Chem. Anal. Ed.*, 17, 787 (1945). Typically, the pore diameters are at least about 0.01 microns (0.01 μm), and more typically, at least about 0.1 μm. Typically, the pore diameters are no more than or less than about 10, 15, 20, 25, 30, 35, 40, 45, or 50 μm. In different embodiments, the pore diameters are about, at least, above, up to, or less than, for example, 0.2 μm, 0.5 μm, 1.0 μm, 1.2 μm, 1.5 μm, 1.8 μm, 2.0 μm, 2.5 μm, 3 μm, 3.5 μm, 4 μm, 4.5 μm, 5 μm, 5.5 μm, 6 μm, 6.5 μm, 7 μm, 7.5 μm, 8 μm, 8.5 μm, 9 μm, 9.5 μm, 10 μm, or 10.5 μm, or the pore diameters are within a range bounded by any two of the foregoing exemplary values. Any range of pore sizes, as particularly derived from any of the above exemplary values, may also contribute any suitable percentage of the total pore volume, such as at least, greater than, up to, or less than, for example, 1, 2, 5, 10, 15, 20, 25, 30, 40, 50, 60, 70, 80, 90, 95, or 98% of the total pore volume. In some embodiments, a range of pore sizes may provide the total (i.e., 100%) pore volume.

In some embodiments, at least 40, 50, 60, 70, 80, or 90% of the pore volume is provided by pores with diameters in a range of 1 to 5 microns. The median pore diameter of the carrier employed may be between about 1 and 5 microns, or between about 1 and 4.5 microns, and or between about 1 and 4 microns. The pore volume from pores with a diameter of 5 microns may be less than about 0.20 mL/g, or less than about 0.10 mL/g, or less than about 0.05 mL/g. The pore volume from pores with a diameter of 1 micron and less may be less than about 0.20 mL/g, or less than about 0.16 mL/g The carrier may possess a pore size distribution (e.g., within a range as set forth above) characterized by the presence of one or more pore sizes of peak concentration, i.e., one or more maxima (where the slope is approximately zero) in a pore size vs. pore volume distribution plot. A pore size of maximum concentration is also referred to herein as a peak pore size, peak pore volume, or peak pore concentration. Furthermore, each pore size distribution can be characterized by a single mean pore size (mean pore diameter) value. Accordingly, a mean pore size value given for a pore size distribution necessarily corresponds to a range of pore sizes that results in the indicated mean pore size value. Any of the exemplary pore sizes provided above can alternatively be understood to indicate a mean (i.e., average or weighted average) or median pore size in a pore size distribution. Any of the exemplary pore sizes provided above may also be interpreted to be the lower and upper bounds of a peak in a pore volume distribution plot.

In a particular embodiment, the carrier possesses a multimodal pore size distribution within any of the pore size ranges described above. The multimodal pore size distribution can be, for example, bimodal, trimodal, or of a higher modality. The multimodal pore size distribution is characterized by the presence of different pore sizes of peak concentration (i.e., different peak pore sizes) in a pore size vs. pore volume distribution plot. The different peak pore sizes are preferably within the range of pore sizes given above. Each peak pore size can be considered to be within its own pore size distribution (mode), i.e., where the pore size concentration on each side of the distribution falls to approximately zero (in actuality or theoretically). In one embodiment, different pore size distributions, each having a peak pore size, are non-overlapping by being separated by a volume concentration of pores of approximately zero (i.e., at baseline). In another embodiment, different pore size distributions, each having a peak pore size, are overlapping by not being separated by a volume concentration of pores of approximately zero. Each mode of pores may contribute any suitable percentage of the total pore volume, such as any of the percentages or ranges thereof, provided above.

The macroscale shape and morphology of the carrier, i.e., after compounding and calcining of the carrier particles, can be any of the numerous shapes and morphologies known in the art. For example, the carrier can be in the form of particles, chunks, pellets, rings, spheres, three-holes, wagon wheels, cross-partitioned hollow cylinders, and the like, of a size preferably suitable for employment in fixed-bed epoxidation reactors. In particular embodiments, the macroscopic carrier units may have equivalent diameters of about, for example, 1, 2, 3, 4, 5, 6, 7, 8, 9, 10, 11, 12, 13, 14, or 15 mm, or an equivalent diameter within a range bounded by any two of the foregoing exemplary values. The equivalent diameter is preferably compatible with the internal diameter of the tubular reactors in which the catalyst is placed. As known in the art, the term "equivalent diameter" is used to express the size of an irregularly-shaped object by expressing the size of the object in terms of the diameter of a sphere having the same volume as the irregularly-shaped object. Alternatively, the equivalent diameter is the diameter of a sphere having the same external surface area (i.e., neglecting surface area within the pores of the particle) to volume ratio as the carrier units being employed.

In order to produce a catalyst for the oxidation of ethylene to ethylene oxide, a carrier having any of the above characteristics is first provided with a catalytically effective amount of silver on its surface. The catalytically effective amount of silver is provided by impregnating the carrier with a silver-containing solution. The carrier can be impregnated with silver and any desired promoters by any of the conventional methods known in the art, e.g., by excess solution impregnation (immersion), incipient wetness impregnation, spray coating, and the like. Typically, the carrier material is placed in contact with the silver-containing solution until a sufficient amount of the solution is absorbed by the carrier. Preferably, the quantity of the silver-containing solution used to impregnate the carrier is no more than is necessary to fill the pore volume of the carrier. Infusion of the silver-containing solution into the carrier can be aided by application of a vacuum.

A single impregnation or a series of impregnations, with or without intermediate drying, may be used, depending in part on the concentration of the silver component in the solution. Impregnation procedures are described in, for example, U.S. Pat. Nos. 4,761,394, 4,766,105, 4,908,343, 5,057,481, 5,187, 140, 5,102,848, 5,011,807, 5,099,041 and 5,407,888, all of which are incorporated herein by reference. Known procedures for pre-deposition, co-deposition, and post-deposition of the various promoters can also be employed.

The silver-containing solution contains silver in ionic form, generally in the form of a silver compound, complex, or salt, dissolved in a suitable solvent. Silver compounds useful for impregnation include, for example, silver oxalate, silver nitrate, silver oxide, silver carbonate, a silver carboxylate, silver citrate, silver phthalate, silver lactate, silver propionate, silver butyrate and higher fatty acid salts and combinations thereof. A wide variety of complexing or solubilizing agents may be employed to solubilize silver to the desired concentration in the impregnating medium. Useful complexing or solubilizing agents include amines, ammonia, lactic acid and combinations thereof. For example, the amine can be an alkylene diamine having from 1 to 5 carbon atoms. In a preferred embodiment, the solution comprises an aqueous solution of silver oxalate and ethylene diamine. The complexing/solubilizing agent may be present in the impregnating solution in an amount from about 0.1 to about 5.0 moles of ethylene diamine per mole of silver, preferably from about 0.2 to about 4.0 moles, and more preferably from about 0.3 to about 3.0 moles of ethylene diamine for each mole of silver.

The silver solution can contain any suitable solvent. The solvent can be, for example, water-based, organic-based, or a combination thereof. In some embodiments, the solvent is or includes water, thereby providing an aqueous silver solution. The solvent can have any suitable degree of polarity, including highly polar, moderately polar or non-polar, or substantially or completely non-polar. The solvent typically has sufficient solvating power to solubilize the solution components. Some examples of water-based solvents include water and water-alcohol mixtures. Some examples of organic-based solvents include, but are not limited to, alcohols (e.g., methanol or ethanol), glycols (e.g., alkyl glycols), ketones, aldehydes, amines, tetrahydrofuran, nitrobenzene, nitrotoluene, glymes (e.g., glyme, diglyme and tetraglyme), and the like, and their combinations. Organic-based solvents that have 1 to about 8 carbon atoms per molecule are preferred.

The concentration of silver salt in the solution is typically in the range from about 0.1% by weight to the maximum permitted by the solubility of the particular silver salt in the solubilizing agent employed. More typically, the concentration of silver salt is from about 0.5, 1, 2, or 5 wt % to 30, 35, 40, or 45 wt % by weight of the impregnating solution.

After impregnation, the excess solution is preferably removed from the impregnated carrier, and the impregnated carrier is then subjected to the two-step calcination process of the present disclosure. The first step of the calcination process is a solvent removal step in which the carrier impregnated with silver-containing solution, generally at ambient temperature (typically about 15-30° C., or more typically 20-25° C.), is heated at or up to a base temperature ($T_{base}$) of at least 80° C. and up to about 200° C. to produce a dry carrier impregnated with ionic silver. In different embodiments, $T_{base}$ is precisely, about, at least, or above, for example, 80, 90, 100, 110, 120, 130, 140, 150, 160, 170, 180, or 190° C., or $T_{base}$ can be selected from a range of temperatures bounded by any two of the foregoing exemplary temperatures (e.g., at least 110, 115, 120, 125, 130, 135, 140, 145, or 150° C. and up to or less than about 150, 160, 170, 180, 190, or 200° C.). The solvent removal step of the calcination process may be conducted in an oxygen-containing or inert environment.

In one set of embodiments, the carrier impregnated with silver-containing solution is heated suddenly at the $T_{base}$ temperature without a gradual increase in temperature from ambient temperature. The sudden change in temperature can be provided by, for example, transferring the carrier impregnated with silver-containing solution to an oven pre-set at a particular $T_{base}$ temperature. The period of time for which the carrier is subjected to the $T_{base}$ temperature can be, for example, at least 1, 2, 5, 10, 15, 20, 30, 40, 50, or 60 minutes, depending on the $T_{base}$ temperature.

In another set of embodiments, the carrier impregnated with silver-containing solution is heated gradually to the $T_{base}$ temperature from ambient temperature. The gradual change in temperature can be provided by, for example, manual or programmed operation of an oven or furnace generally used in the art. The gradual increase in temperature can correspond to any suitable temperature ramp rate, typically at least 1° C./min and up to 40° C./min. In different embodiments, the temperature ramp rate for the solvent removal step is precisely, about, at least, above, up to, or less than, for example, 1, 2, 3, 4, 5, 6, 7, 8, 9, 10, 12, 15, 18, 20, 22, 25, 28, 30, 32, 35, 38, or 40° C./min, or a temperature ramp rate within a range bounded by any two of the foregoing exemplary values. In some embodiments, the temperature ramp rate is selected so as to reach a desired $T_{base}$ temperature in a specified amount of time. The specified amount of time may be, in particular embodiments, precisely, about, or at least 5, 10, 12, 15, 18, 20, 25, 30, 40, 50, or 60 minutes.

The second step of the calcination process, which follows the solvent removal step, is a silver reduction step in which the dry silver-impregnated carrier is gradually heated above the base temperature under an inert atmosphere (e.g., nitrogen or argon) to a maximum temperature ($T_{max}$) of at least 350° C. and up to about 500° C. and then gradually cooled to the base temperature. In different embodiments, $T_{max}$ is precisely, about, at least, or above, for example, 350, 360, 370, 380, 390, 400, 410, 420, 430, 440, 450, 460, 470, 480, or 490° C., or $T_{max}$ can be selected from a range of temperatures bounded by any two of the foregoing exemplary temperatures (e.g., at least 350, 360, 370, 380, 390, 400, 410, 420, 430, 440, or 450° C. and up to or less than about 450, 460, 470, 480, 490, or 500° C.). The atmosphere under which the second step of the calcination process is conducted may also include a reducing agent (e.g., hydrogen), or a separate chemical reduction step may be conducted before or after the second calcination step.

In the second step of the calcination process, the dried silver-impregnated carrier is gradually elevated in temperature from the $T_{base}$ temperature to the $T_{max}$ temperature. The gradual increase in temperature can correspond to any suitable temperature ramp rate, typically at least 1° C./min and up to 40° C./min, and can be, independently, any of the exemplary temperature ramp rates provided above for the solvent removal step. In some embodiments, the temperature ramp rate for the silver reduction step is selected so as to reach a desired $T_{max}$ temperature in a specified amount of time. The specified amount of time may be, in particular embodiments, precisely, about, or at least 5, 10, 12, 15, 18, 20, 25, 30, 40, 50, or 60 minutes.

The second step of the calcination process also includes gradually cooling the dried silver-impregnated carrier from the $T_{max}$ temperature to the $T_{base}$ temperature or a lower temperature. Generally, the dried silver-impregnated carrier is cooled back to ambient temperature. The gradual decrease in temperature can correspond to any suitable temperature ramp rate, which can be any of the temperature ramp rates provided above, but in the negative direction. Moreover, the temperature ramp rate employed in reaching $T_{max}$ may be the same, approximately the same, or different than the temperature ramp rate employed in decreasing the temperature from $T_{max}$ back to $T_{base}$ or a lower temperature.

Figure 1:
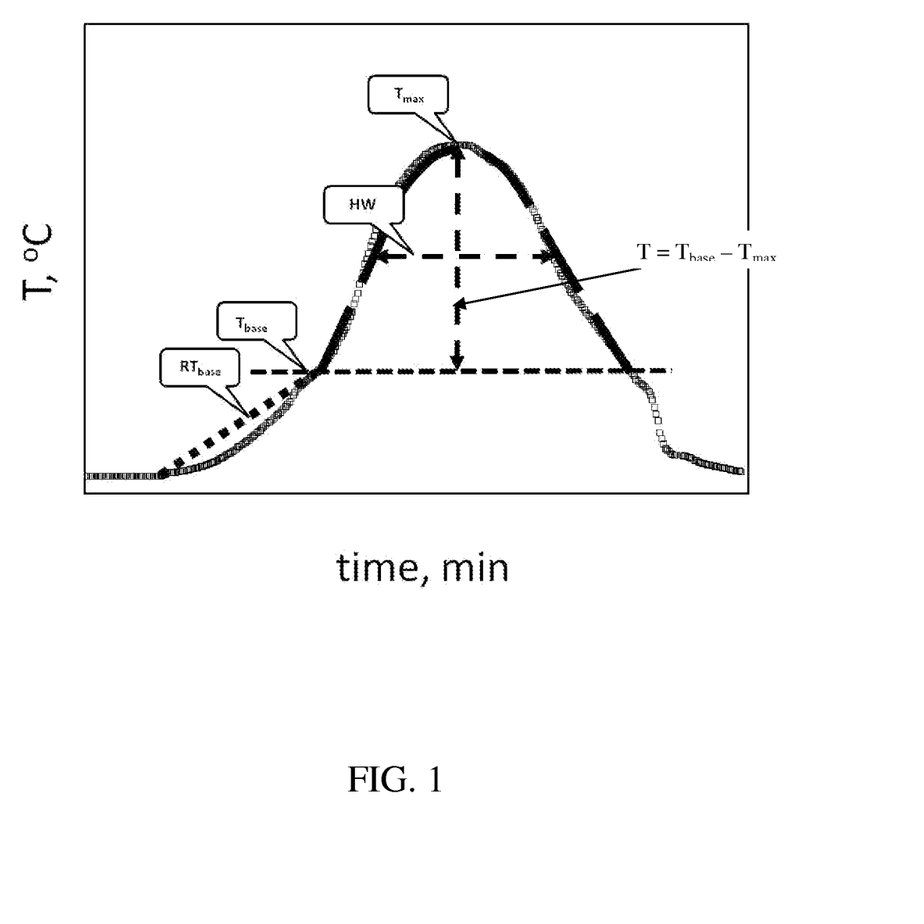
FIG. 1 is a drawing depicting the basic parameters of the calcination temperature-vs-time profile.

The second calcination step, by gradually increasing to a peak temperature ($T_{max}$) and gradually decreasing from $T_{max}$ back to $T_{base}$, necessarily defines a curve (peak) when temperature is plotted as a function of time on a temperature-vs-time plot. A generic and purely exemplary form of such a curve is provided in FIG. 1, wherein $T_{base}$ is the maximum temperature used in the solvent removal step; $RT_{base}$ is defined as the amount of time used in ramping the temperature from ambient temperature to $T_{base}$ (alternatively, no ramping of temperature is used in the solvent removal step, as discussed above, in which case $RT_{base}$ is simply defined as the residence time at a temperature $T_{base}$); $T_{max}$ is the peak (maximum) temperature used in the silver reduction step; T is defined as $T_{base}-T_{max}$; and HW is the full width at half maximum (half-width) of the curve with $T_{base}$ taken as the base of the curve.

The instant disclosure provides the surprising result that particular combinations of T and HW result in a catalyst improved in activity, selectivity, and/or stability. In particular embodiments, the second step of the calcination process is conducted such that the product of T and HW, i.e., ($T_{base}-T_{max}$)×HW, is at least 2000 min.° C., wherein $T_{base}$ and $T_{max}$ are measured in ° C., and HW is measured in minutes. In different embodiments, ($T_{base}-T_{max}$)×HW is about or at least 2000, 2500, 3000, 3500, 4000, 4500, 5000, 5500, 6000, 6500, 7000, 7500, 8000, 8500, or 9000 min.° C., or ($T_{base}-T_{max}$)× HW is within a range bounded by any two of the foregoing values.

After calcining the high selectivity catalyst, the calcined catalyst is typically loaded into reactor tubes of an epoxidation reactor, typically a fixed bed tubular reactor, utilizing conventional loading methods well known to those skilled in the art. After loading, the catalyst bed may be swept by passing an inert gas such as nitrogen over the catalyst bed.

The produced catalyst preferably exhibits a selectivity of at least 85% for the conversion of ethylene to ethylene oxide. In different embodiments, the produced catalyst exhibits a selectivity of about or at least, for example, 85%, 86%, 87%, 88%, 89%, 90%, 91%, 92%, or 93% or a selectivity within a range bounded by any two of the foregoing values.

The produced catalyst contains a catalytically effective amount of silver metal to catalyze the synthesis of ethylene oxide from ethylene and oxygen. The silver can be located on the surface and/or throughout the pores of the refractory support. A catalytically effective amount of silver can be, for example, up to about 45% by weight of silver, expressed as metal, based on the total weight of the catalyst including the carrier. Silver contents, expressed as metal, of from about 1% to about 40% based on the total weight of the catalyst are more typical. In other embodiments, the silver content can be from, for example, about 1 to 35%, 5 to 35%, 1 to 30%, 5 to 30%, 1 to 25%, 5 to 25%, 1 to 20%, 5 to 20%, 8 to 40%, 8 to 35%, 8 to 30%, 10 to 40%, 10 to 35%, 10 to 25%, 12 to 40%, 12 to 35%, 12 to 30%, or 12 to 25%.

The produced catalyst may also contain one or more promoting species. As used herein, a "promoting amount" of a certain component of a catalyst refers to an amount of that component that works effectively to provide an improvement in one or more of the catalytic properties of the catalyst when compared to a catalyst not containing said component. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement is exhibited in the activity rather than in the selectivity. All of the promoters, aside from the alkali metals, can be in any suitable form, including, for example, as zerovalent metals or higher valent metal ions.

For example, the produced catalyst may include a promoting amount of an alkali metal or a mixture of two or more alkali metals. Suitable alkali metal promoters include, for example, lithium, sodium, potassium, rubidium, cesium or combinations thereof. Cesium is often preferred, with combinations of cesium with other alkali metals also being preferred. The amount of alkali metal will typically range from about 10 ppm to about 3000 ppm, more typically from about 15 ppm to about 2000 ppm, more typically from about 20 ppm to about 1500 ppm, and even more typically from about 50 ppm to about 1000 ppm by weight of the total catalyst, expressed in terms of the alkali metal.

The produced catalyst may also include a promoting amount of a Group IIA alkaline earth metal or a mixture of two or more Group IIA alkaline earth metals. Suitable alkaline earth metal promoters include, for example, beryllium, magnesium, calcium, strontium, and barium or combinations thereof. The amounts of alkaline earth metal promoters can be used in amounts similar to those used for the alkali or transition metal promoters.

The produced catalyst may also include a promoting amount of a main group element or a mixture of two or more main group elements. Suitable main group elements include any of the elements in Groups IIIA (boron group) to VIIA (halogen group) of the Periodic Table of the Elements. For example, the carrier or catalyst can include a promoting amount of sulfur, phosphorus, boron, halogen (e.g., fluorine), gallium, or a combination thereof. The main group element may be present in the form of a compound. Aside from the halogens, the main group element may be present in its elemental form.

The produced catalyst may also include a promoting amount of a transition metal or a mixture of two or more transition metals. Suitable transition metals can include, for example, the elements from Groups IIIB (scandium group), IVB (titanium group), VB (vanadium group), VIB (chromium group), VIIB (manganese group), VIIIB (iron, cobalt, nickel groups), IB (copper group), and IIB (zinc group) of the Periodic Table of the Elements, as well as combinations thereof. More typically, the transition metal is an early transition metal, i.e., from Groups IIIB, IVB, VB or VIB, such as, for example, hafnium, yttrium, molybdenum, tungsten, rhenium, chromium, titanium, zirconium, vanadium, tantalum, niobium, or a combination thereof. In one embodiment, the transition metal promoter is present in an amount from about 10 ppm to about 1000 ppm of total carrier or catalyst expressed as the metal. In another embodiment, the transition metal promoter is present in an amount from about 20 ppm to about 500 ppm of total carrier or catalyst expressed as the metal. In a further embodiment, the transition metal promoter is present in an amount from about 30 ppm to about 350 ppm of total carrier or catalyst expressed as the metal. Alternatively, the transition metal can be present in an amount of from about 0.1 micromoles per gram to about 10 micromoles per gram, more typically from about 0.2 micromoles per gram to about 5 micromoles per gram, and even more typically from about 0.5 micromoles per gram to about 4 micromoles per gram of the carrier or silver-containing catalyst, expressed in terms of the metal.

Of the transition metal promoters listed, rhenium (Re) is preferred as a particularly efficacious promoter for ethylene epoxidation high selectivity catalysts. The rhenium component in the carrier or catalyst can be in any suitable form, but is more typically one or more rhenium-containing compounds (e.g., a rhenium oxide) or complexes. The rhenium can be present in an amount of, for example, about 0.001 wt. % to about 1 wt. %. More typically, the rhenium is present in amounts of, for example, about 0.005 wt. % to about 0.5 wt. %, and even more typically, from about 0.01 wt. % to about 0.05 wt. % based on the weight of the total carrier, or by weight of the catalyst including the carrier, expressed as rhenium metal.

The produced catalyst may also include a promoting amount of a rare earth metal or a mixture of two or more rare earth metals. The rare earth metals include any of the elements having an atomic number of 57-103. Some examples of these elements include lanthanum (La), cerium (Ce), and samarium (Sm). The amount of rare earth metal promoters can be used in amounts similar to those used for the transition metal promoters.

In a first set of embodiments, the carrier, before impregnation, contains one or more of any of the promoters described above. In a second set of embodiments, the carrier is provided with one or more promoters during silver impregnation with the silver-containing solution. In the latter embodiment, the carrier, before silver impregnation, may or may not contain any or all of the promoters described above. In a third set of embodiments, the carrier, after silver impregnation and calcination, is provided with one or more promoters in a post-processing step. In the latter embodiment, the carrier, before impregnation or calcination, may or may not contain any or all of the promoters described above.

In another aspect, the instant disclosure is directed to a method for the vapor phase production of ethylene oxide by conversion of ethylene to ethylene oxide in the presence of oxygen by use of the catalyst described above. Generally, the ethylene oxide production process is conducted by continuously contacting an oxygen-containing gas with ethylene in the presence of the catalyst at a temperature in the range from about 180° C. to about 330° C., more typically from about 200° C. to about 325° C., and more typically from about 225° C. to about 270° C., at a pressure which may vary from about atmospheric pressure to about 30 atmospheres depending on the mass velocity and productivity desired. Pressures in the range of from about atmospheric to about 500 psi are generally employed. Higher pressures may, however, be employed within the scope of this disclosure. Residence times in large-scale reactors are generally on the order of about 0.1 to about 5 seconds. A typical process for the oxidation of ethylene to ethylene oxide comprises the vapor phase oxidation of ethylene with molecular oxygen in the presence of the inventive catalyst in a fixed bed, tubular reactor. Conventional commercial fixed bed ethylene oxide reactors are typically in the form of a plurality of parallel elongated tubes (in a suitable shell). In one embodiment, the tubes are approximately 0.7 to 2.7 inches O.D. and 0.5 to 2.5 inches I.D. and 15-45 feet long filled with catalyst.

The inventive catalysts are particularly active and selective in the conversion of ethylene to ethylene oxide. The conditions for conducting such an oxidation reaction in the presence of the catalyst herein described broadly comprise those described in the prior art. This applies, for example, to suitable temperatures, pressures, residence times, diluent materials (e.g., nitrogen, carbon dioxide, steam, argon, methane or other saturated hydrocarbons), the presence or absence of moderating agents to control the catalytic action (e.g., 1,2-dichloroethane, vinyl chloride or ethyl chloride), the desirability of employing recycle operations or applying successive conversion in different reactors to increase the yields of ethylene oxide, and other particular conditions that may be beneficial for converting ethylene to ethylene oxide. Molecular oxygen employed as a reactant may be obtained from conventional sources, and may be relatively pure oxygen, or a concentrated oxygen stream comprising oxygen in a major amount with lesser amounts of one or more diluents such as nitrogen or argon, or air.

In other embodiments, the process of ethylene oxide production includes the addition of oxidizing gases to the feed to increase the efficiency of the process. For example, U.S. Pat. No. 5,112,795 discloses the addition of 5 ppm of nitric oxide to a gas feed having the following general composition: 8 volume % oxygen, 30 volume % ethylene, about 5 ppmw ethyl chloride, with the balance as nitrogen.

In the production of ethylene oxide, reactant feed mixtures typically contain from about 0.5 to about 45% ethylene and from about 3 to about 15% oxygen, with the balance comprising comparatively inert materials including such substances as nitrogen, carbon dioxide, methane, ethane, argon and the like. Only a portion of the ethylene is typically reacted per pass over the catalyst. After separation of the desired ethylene oxide product and removal of an appropriate purge stream and carbon dioxide to prevent uncontrolled build up of inert products and/or byproducts, unreacted materials are typically returned to the oxidation reactor. For purposes of illustration only, the following are conditions that may be used in a conventional industrial ethylene oxide reactor unit: a gas hourly space velocity (GHSV) of 1500-10,000 $h^{-1}$, a reactor inlet pressure of 150-400 psig, a coolant temperature of 180-315° C., an oxygen conversion level of 10-60%, and an EO production (work rate) of 100-300 kg EO per cubic meters of catalyst per hour. Typically, the feed composition at the reactor inlet comprises 1-40% ethylene, 3-12% oxygen, 0.3-40% $CO_2$, 0-3% ethane, 0.3-20 ppmv total concentration of organic chloride moderator, with the balance of the feed being argon, methane, nitrogen, or mixtures thereof.

Some examples of organic chloride moderators that can be employed in the present disclosure include, for example, organic halides, such as $C_1$ to $C_8$ halohydrocarbons, which, may be, for example, methyl chloride, ethyl chloride, ethylene dichloride, vinyl chloride, or a mixture thereof. Also suitable are hydrogen-free chlorine sources, such as perhalogenated hydrocarbons and diatomic chlorine, both of which are particularly effective as moderators in gas phase epoxidation. Perhalogenated hydrocarbons refer to organic molecules in which all of the hydrogen atoms in a hydrocarbon have been substituted with halogen atoms. Some examples of perhalogenated hydrocarbons include trichlorofluoromethane and perchloroethylene. The concentration of the moderator should be controlled so as to balance a number of competing performance characteristics. For example, moderator concentration levels that result in improved activity may simultaneously lower selectivity. Controlling moderator concentration level is particularly important with rhenium-containing catalysts of the present disclosure, because as the rhenium-containing catalysts age, the moderator concentration must be carefully monitored so as to continually increase, within small increments, since optimal selectivity values are obtained only within a narrow moderator concentration range.

The resulting ethylene oxide is separated and recovered from the reaction products using methods known in the art. The ethylene oxide process may include a gas recycle process wherein a portion or substantially all of the reactor effluent is readmitted to the reactor inlet after substantially removing the ethylene oxide product and byproducts. In the recycle mode, carbon dioxide concentrations in the gas inlet to the reactor may be, for example, about 0.3 to about 6 volume percent, and more typically, about 0.3 to about 2.0 volume percent.

Examples have been set forth below for the purpose of further illustrating the invention. The scope of this invention is not to be in any way limited by the examples set forth herein.

EXAMPLES

Preparation of Silver Impregnation Solution

Stock Solution for HSC: 277.5 g of deionized water was placed in a cooling bath to maintain temperature during the whole preparation under 50° C. With continuous stirring, 221.9 g of ethylenediamine (99+%, Aldrich) was added in small portions to avoid overheating. 174.1 g of oxalic acid dehydrate (ACS Certified Reagent, Fisher) was then added to the water-ethylenediamine solution in small portions. After all oxalic acid dissolved, 326.5 g of high purity silver oxide (Ames Goldsmith Corp.) was added to the solution in small portions. After all silver oxide dissolved, the solution was cooled to approximately 35° C. and removed from the cooling bath. After filtration, the solution contained roughly 30 wt % silver, and had a specific gravity of 1.55 g/mL.

Silver Impregnation Process

A conventional alpha-alumina carrier was used, with a surface area, water absorption, and other properties within the scope of the present disclosure. A 150 g portion of the alpha-alumina carrier was placed in a flask and evacuated to about 0.1 Torr prior to impregnation. To the above silver solution were added aqueous solutions of 17 wt % Cs as cesium hydroxide, 3.8 wt % Re as ammonium perrhenate, 4 wt % Li as $LiNO_3$, 4 wt % W as ammonium metatungstate, and 5 wt % S as ammonium sulfate in order to prepare a catalyst composition. After thorough mixing, the promoted silver solution was aspirated into the evacuated flask to cover the carrier while maintaining the pressure at about 0.1 Torr. The vacuum was released after about five minutes to restore ambient pressure, hastening complete penetration of the solution into the pores. Excess impregnation solution was drained from the impregnated carrier.

Calcination Process

Figure 2:
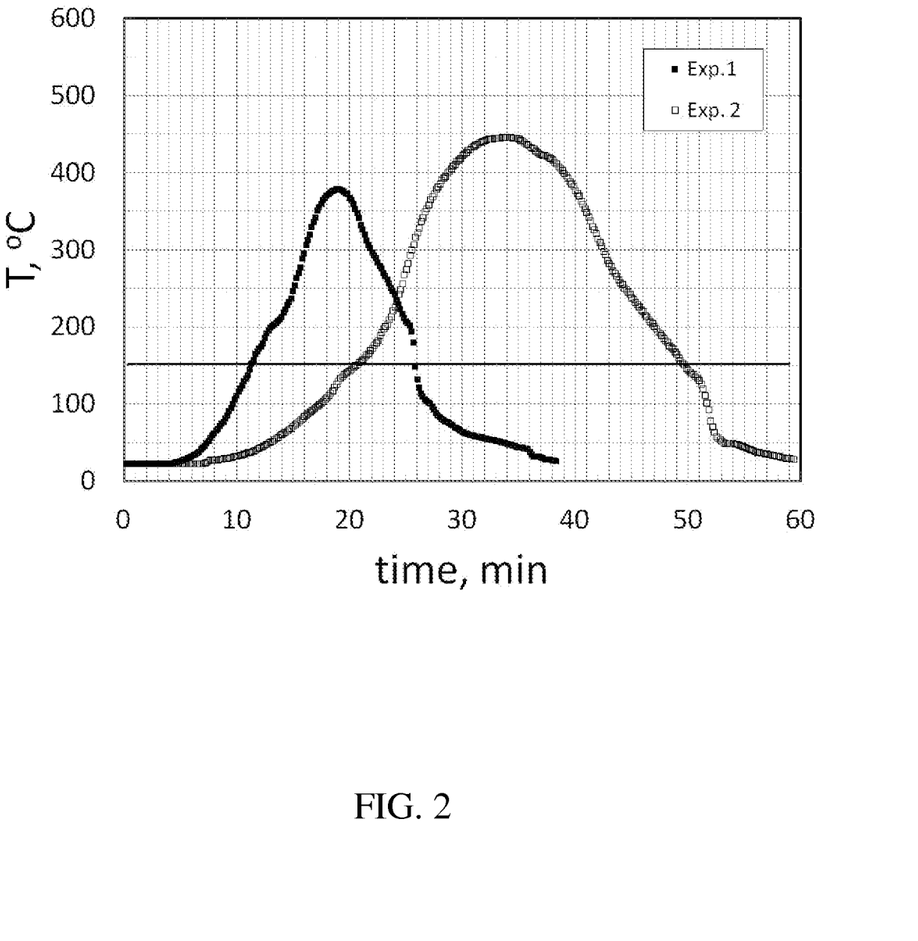
FIG. 2 is a graph showing two different calcination temperature profiles (Experiments 1 and 2) used on silver-impregnated carriers of the same composition.

The carrier impregnated with liquid silver-containing solution, produced as above, was subjected to an exemplary two-step calcination process, as more generally described above, to produce a high selectivity catalyst (HSC). Calcination of the wet catalyst was conducted on a moving belt calciner. In this unit, the wet catalyst entered the furnace at ambient temperature and was transported on a stainless steel belt through a multi-zone furnace. All zones of the furnace were continuously purged with pre-heated, ultra-high purity nitrogen and the temperature of the zones were set to specific levels to increase the catalyst temperature gradually to the target level as the catalyst passed from one zone to the next. The heat was radiated from the furnace walls and from the preheated nitrogen. In the last (cooling) zone, the temperature of the now activated HSC was quickly lowered to less than 100° C. before it emerged into ambient atmosphere. FIG. 2 presents actual temperature profiles collected from the travelling thermocouple embedded into the calcined catalyst. In addition to varying the temperatures of the furnace zones, the speed of the belt was also varied to achieve different rates of temperature rise from ambient to $T_{base}=150°$ C., $T_{max}$, and $(T_{base}-T_{max}) \times HW$ of calcinations.

Ethylene Oxide Production Process

Figure 3A:
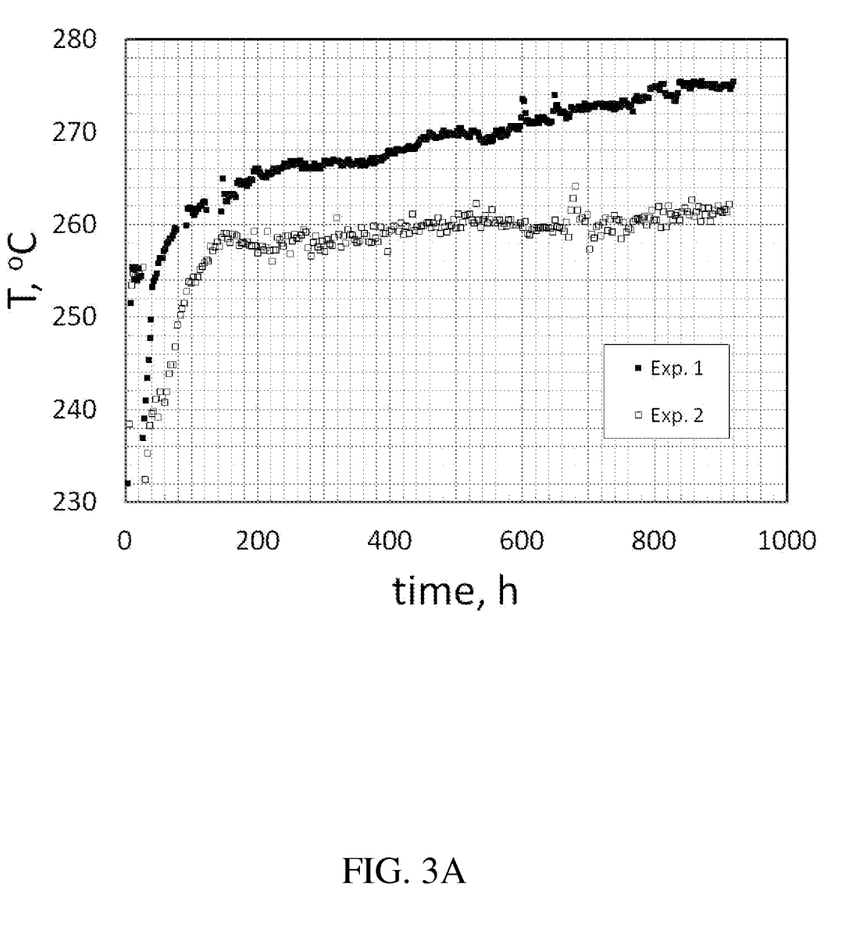
FIGS. 3A and 3B are graphs showing activity (FIG. 3A) and selectivity (FIG. 3B) performance as a function of time for the two catalysts produced by the two calcination temperature profiles shown in FIG. 2.
Figure 3B:
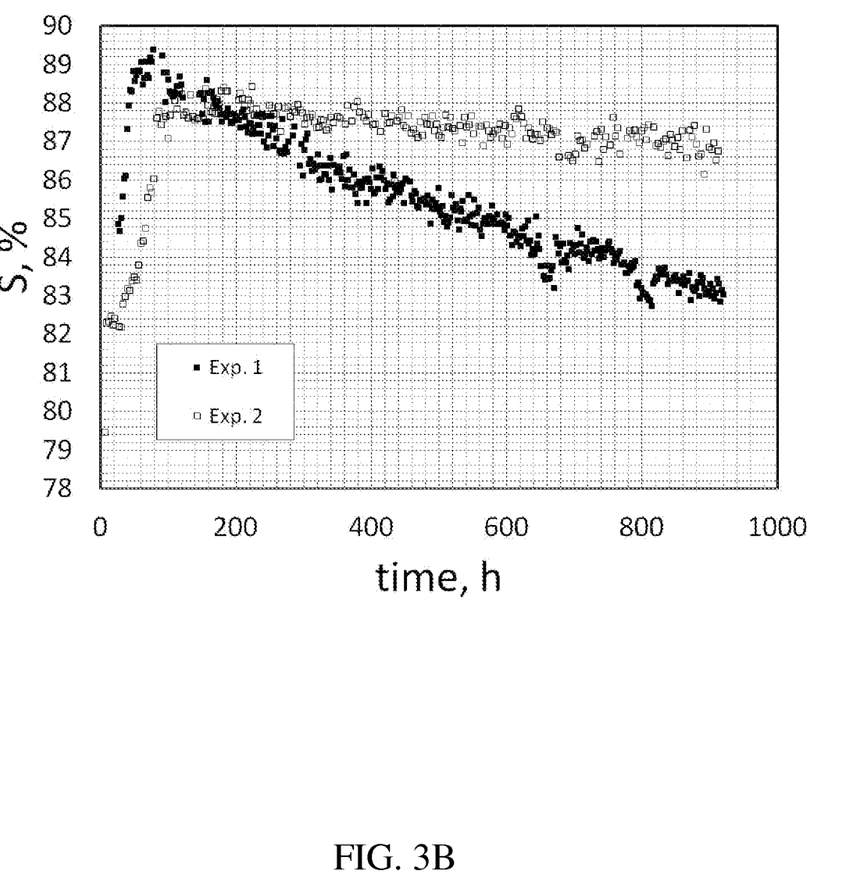

The two high selectivity catalysts, produced as above, were tested for their ability to convert ethylene to ethylene oxide under conventional industrial conditions. The catalysts were tested in heated stainless steel tubes at a pressure of 300 psig. The catalysts were conditioned before target operating conditions were set. Notably, the following conditioning procedure was followed for each catalyst. After loading the catalyst, nitrogen was passed through the reactor. Under the flow of nitrogen, the temperature of the reactor was raised from ambient to 225° C. in two to three hours. Upon reaching 225° C., the feed containing 8% $C_2H_4$, 4% $O_2$, 4% $CO_2$ and 2 ppm ethyl chloride in a nitrogen ballast was introduced. As feed was introduced, the temperature started to rise at a ramp of 5° C./h to the target activation temperature of 255° C. The catalyst was held at this temperature for 15-18 hours after which it was reduced to 230-235° C., feed was changed to operation feed of 25% $C_2H_4$, 7% $O_2$, 2% $CO_2$, and chloride level was reduced to 1.5 ppm. As the reaction continued, chloride was further optimized to achieve a maximum selectivity at minimum temperature at target weight work rate (WWR) of 523. FIG. 3A demonstrates that the catalyst after calcination Experiment 2 was more active at the start of the run and had better activity stability than the catalyst after Experiment 1. FIG. 3B shows that the catalyst after calcination Experiment 2 had lower maximum selectivity at the start of run but had much better selectivity stability and better selectivity after 200 hours of the test.

While there have been shown and described what are presently believed to be the preferred embodiments of the present disclosure, those skilled in the art will realize that other and further embodiments can be made without departing from the spirit and scope of the present disclosure, and this disclosure includes all such modifications that are within the intended scope of the claims set forth herein.

What is claimed is:

1. A method for producing a catalyst effective in the oxidative conversion of ethylene to ethylene oxide, the method comprising:
    subjecting a refractory carrier impregnated with a liquid silver-containing solution to a two-step calcination process, wherein the two-step calcination process comprises:
        removing solvent, in a first step, from the silver-impregnated carrier, wherein the removing is performed by heating the silver-impregnated carrier to a base temperature ($T_{base}$) of at least 80° C. and up to about 200° C. to produce a dry carrier impregnated with ionic silver, and
        reducing ionic silver, in a second step, from the dry carrier impregnated with ionic silver by gradually heating the dry carrier above the base temperature under an inert atmosphere to a maximum temperature ($T_{max}$) of at least 350° C. and up to about 500° C. and then gradually cooling to the base temperature, wherein the two-step calcination process is conducted such that $(T_{base}-T_{max}) \times HW$ is at least 2000 min.° C.,
    wherein $T_{base}$ and $T_{max}$ are measured in ° C., and HW is measured in minutes and is a full width at half maximum of a temperature versus time curve delineated by the second step of reducing ionic silver where $T_{base}$ is taken as the baseline of the curve in calculating HW.

2. The method of claim 1, wherein $T_{base}$ is at least 110° C. and up to about 180° C.

3. The method of claim 1, wherein $T_{base}$ is at least 140° C. and up to about 160° C.

4. The method of claim 1, wherein said removing said solvent is conducted for at least five minutes.

5. The method of claim 1, wherein said removing said solvent is conducted for at least 10 minutes.

6. The method of claim 1, wherein said removing said solvent is conducted by gradually heating the impregnated carrier at a temperature ramp rate of up to 10° C./min from ambient temperature to a base temperature of at least 110° C. and up to about 180° C.

7. The method of claim 1, wherein $T_{max}$ is at least 390° C. and up to about 480° C.

8. The method of claim 1, wherein $T_{max}$ is at least 430° C. and up to about 460° C.

9. The method of claim 1, wherein $(T_{base}-T_{max}) \times HW$ is up to about 7000 min.° C.

10. The method of claim 1, wherein $(T_{base}-T_{max}) \times HW$ is up to about 6500 min.° C.

11. The method of claim 1, wherein $(T_{base}-T_{max}) \times HW$ is at least 3000 min.° C.

12. The method of claim 1, wherein $(T_{base}-T_{max}) \times HW$ is at least 4000 min.° C.

13. The method of claim 1, wherein $(T_{base}-T_{max}) \times HW$ is in a range of at least 3000 and up to about 6000 min.° C.

14. The method of claim 1, wherein $(T_{base}-T_{max}) \times HW$ is in a range of at least 4000 and up to about 6000 min.° C.

15. The method of claim 1, wherein the catalyst exhibits a selectivity of at least 86%.

16. The method of claim 1, wherein said removing said solvent is conducted under an inert atmosphere.

17. The method of claim 1, wherein the refractory carrier is comprised of alumina.

18. The method of claim 17, wherein said alumina is alpha-alumina.

19. The method of claim 1, further comprising, before the two-step calcination process, preparing the refractory carrier impregnated with silver solution by depositing a catalytically effective amount of silver as silver solution onto or into the refractory carrier.

20. The method of claim 19, wherein the refractory carrier is immersed into the silver solution.

21. The method of claim 1, wherein the liquid silver-containing solution comprises a silver salt dissolved in a solvent.

22. The method of claim 21, wherein the liquid silver-containing solution further comprises a promoting amount of an element selected from alkali, alkaline earth, and transition metals.

23. The method of claim 21, wherein the liquid silver-containing solution further comprises rhenium.

24. The method of claim 21, wherein the liquid silver-containing solution further comprises cesium.

* * * * *